(12) United States Patent
Soga et al.

(10) Patent No.: US 7,226,438 B2
(45) Date of Patent: Jun. 5, 2007

(54) DISPOSABLE WEARING ARTICLE

(75) Inventors: Hiroyuki Soga, Kagawa-ken (JP); Satoru Tange, Kagawa-ken (JP); Yuko Matsuda, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/334,533

(22) Filed: Jan. 19, 2006

(65) Prior Publication Data

US 2006/0161128 A1    Jul. 20, 2006

(30) Foreign Application Priority Data

Jan. 19, 2005   (JP)   ............... 2005-012079

(51) Int. Cl.
*A61F 13/15* (2006.01)
(52) U.S. Cl. .................. 604/385.25; 604/385.01; 604/385.27
(58) Field of Classification Search .......... 604/385.25, 604/385.27, 387, 391, 385.01, 385.28
See application file for complete search history.

(56) References Cited

U.S. PATENT DOCUMENTS

| | | | | |
|---|---|---|---|---|
| 5,188,627 A | * | 2/1993 | Igaue et al. ............ | 604/385.27 |
| 5,766,212 A | * | 6/1998 | Jitoe et al. ............... | 604/361 |
| 5,836,931 A | * | 11/1998 | Toyoda et al. ............ | 604/358 |
| 5,897,541 A | * | 4/1999 | Uitenbroek et al. ...... | 604/358 |
| 2004/0133181 A1 | * | 7/2004 | Ishiguro et al. ......... | 604/385.28 |

FOREIGN PATENT DOCUMENTS

| | | |
|---|---|---|
| EP | 1 062 930 A2 | 12/2000 |
| JP | 10-57410 | 3/1998 |
| JP | 10-277091 | 10/1998 |

* cited by examiner

*Primary Examiner*—Tatyana Zalukaeva
*Assistant Examiner*—Ginger Chapman
(74) *Attorney, Agent, or Firm*—Lowe Hauptman & Berner LLP

(57) ABSTRACT

A disposable wearing article includes a backsheet which is composed of inner and outer sheets and a light transmission in a region of the backsheet in which the inner and outer sheets are placed upon each other is in a range of 20 to 50%. First and second elastic members constituting leg elastic members are colored in substantially the same white or milky white as that of the inner and outer sheets and respective intermediate segments of these elastic members are sandwiched between a liquid-absorbent layer and the inner sheet. The inner and outer sheets conceal the respective intermediate segments of these elastic members so that the respective intermediate segments of the elastic members are not highly visible and the article is protected from any deterioration of its appearance.

18 Claims, 8 Drawing Sheets

DISPOSABLE WEARING ARTICLE

RELATED APPLICATIONS

The present application is based on, and claims priority from, Japanese Application Number 2005-12079, filed Jan. 19, 2005, the disclosure of which is hereby incorporated by reference herein in its entirety.

BACKGROUND OF THE INVENTION

The present invention relates to a disposable wearing article for absorption and retention of bodily waste.

There has already been provided a disposable wearing article comprising a liquid-pervious topsheet facing the wearer's skin, a liquid-impervious backsheet facing away from the wearer's skin and a liquid-absorbent layer sandwiched between the top- and backsheets so as to define a front waist region, a rear waist region and a crotch region extending between these waist regions. The article is contoured by longitudinally opposite ends extending in a transverse direction and transversely opposite edges extending in a longitudinal direction. The article includes a plurality of waist elastic members attached to the longitudinally opposite ends in a stretchable/contractible manner and a plurality of leg elastic members attached to the transversely opposite edges of the crotch region in a stretchable/contractible manner (See PATENT DOCUMENT 1). In this article of prior art, the front waist region and the rear waist region are put flat together along the transversely opposite edges of the respective waist regions and these edges put flat together are permanently bonded together at a plurality of heat-sealing lines arranged intermittently along the respective edges of these waist regions. This article of prior art is of pants-type having a waist-hole and a pair of leg-holes.

The waist elastic members are sandwiched between the top- and backsheets and stretched at a predetermined ratio to be bonded to these sheets in such stretched state. The leg elastic members comprise first elastic members extending from the side of the front waist region into the crotch region so as to be convex toward a middle zone of the crotch region and second elastic members extending from the side of the rear waist region into the crotch region so as to be convex toward the middle zone of the crotch region. The first elastic members comprise transversely opposite lateral segments and intermediate segments extending between these lateral segments across the middle zone of the crotch region. The second elastic members comprise transversely opposite lateral segments and intermediate segments extending between these lateral segments across the middle zone of the crotch region. The lateral segments of the first and second elastic members are sandwiched between the top- and backsheets and permanently bonded to these sheets. The intermediate segments of the first and second elastic members comprise crossover sites lying immediately outside transversely opposite sides of the liquid-absorbent layer and intersecting one another and cross segments extending between the crossover sites across the liquid-absorbent layer. The crossover sites are sandwiched between the top- and backsheets and permanently bonded to these sheets. The cross segments are sandwiched between the backsheet and the liquid-absorbent layer and permanently bonded to these sheet and layer. The lateral segments as well as the intermediate segments of the first and second elastic members are stretched at a predetermined ratio and permanently bonded in such stretched state to the respective sheets and layer. The first and second elastic members are relaxed immediately after the lateral segments and the intermediate segments have been permanently bonded to the respective sheets and layer.

[PATENT DOCUMENT 1] Japanese Laid-open Patent Application Gazette No. 1998-57410

In the case of the wearing article disclosed in PATENT DOCUEMENT 1, if a light transmission of the backsheet is relatively high, color of the respective intermediate segments of the first and second elastic members will be transmitted through the backsheet and consequentially the intermediate segment may be seen through the backsheet from the outside of the backsheet. If a stretch ratio of the respective intermediate segments of the first and second elastic members is relatively high, a contractile force of the intermediate segments may cause the backsheet as well as the liquid-absorbent layer to contract in the transverse direction and thereby cause the backsheet as well as the liquid-absorbent layer extending in the crotch region to be formed with a plurality of irregular wrinkles. If the respective intermediate segments of the first and second elastic members are seen through the backsheet and the contractile force of the intermediate segments causes the backsheet to be formed with such wrinkles, the respective intermediate segments of the elastic members extending in the crotch region as well as the wrinkles of the backsheet will be highly visible and the appearance of the article will be deteriorated.

SUMMARY OF THE INVENTION

In view of the problem as has been described above, it is a principal object of the present invention to provide a disposable wearing article improved so that the intermediate segments of the first and second elastic members are not highly visible in the crotch region, the backsheet is not readily formed with wrinkles in the crotch region and deterioration of the article's appearance can be reliably prevented.

The object set forth above is achieved, according to the present invention, by an improvement in the disposable wearing article comprises the following features:

a topsheet facing the wearer's skin, a backsheet facing away from the wearer's skin; a liquid-absorbent layer sandwiched between the top- and backsheets; front and rear waist regions and a crotch region extending between these waist regions; longitudinally opposite ends extending in a transverse direction and transversely opposite edges extending in a longitudinal direction; transversely opposite edges of the crotch region being provided with leg elastic members attached in a stretchable/contractible manner, the leg elastic members comprising first elastic members extending from a side of the front waist region into the crotch region so as to be convex toward a middle zone of the crotch region and second elastic members extending from a side of the rear waist region into the crotch region so as to be convex toward the middle zone of the crotch region, and the first elastic members having transversely opposite lateral segments and intermediate segments extending between the lateral segments across the crotch region, and the second elastic members having transversely opposite lateral segments and intermediate segments extending between the lateral segments across the crotch region.

The improvement according to the present invention further comprises the backsheet being composed of an inner sheet facing the liquid-absorbent layer and extending in the front and rear waist regions and the crotch region or at least the crotch region and an outer sheet extending on an outside of the inner sheet between the front and rear waist regions, a region of the backsheet in which the inner and outer sheets are placed upon each other having a light transmission in a range of 20 to 50%, and the respective intermediate segments of the first and second elastic members being sandwiched between the liquid-absorbent layer and the inner sheet.

According to one preferred embodiment of the invention, color of the first and second elastic members is substantially the same as that of the inner and outer sheets and a color difference between the inner sheet and the first and second elastic members is in a range of 10 to 30.

According to another preferred embodiment of the invention, a stretch ration of the respective intermediate segments of the first and second elastic members is in a range of 1.1 to 1.3.

According to still another preferred embodiment of the invention, the respective intermediate segments of the first and second elastic members are left free from the liquid-absorbent layer.

According to further another preferred embodiment of the invention, the inner and outer sheets are formed from one of a moisture-pervious but liquid-impervious plastic film and a hydrophobic fibrous nonwoven fabric.

In the disposable wearing article according to this invention, the light transmission in the region in which the inner and outer sheets constituting the backsheet are placed upon each other is in a range of 20 to 50% and the respective intermediate segments of the first and second elastic members are sandwiched between the liquid-absorbent layer and the inner sheet. Such arrangement makes it difficult for the color of the respective intermediate segments of the elastic members to be transmitted through the backsheet and thereby to be seen through the backsheet from the outside. In the crotch region, the respective intermediate segments of the first and second elastic members are not highly visible and there is no anxiety that the appearance of the article might be deteriorated.

In the wearing article implemented so that the first and second elastic members have substantially the same color as that of the inner and outer sheets and a color difference between the inner sheet and the first and second elastic members is in a range of 10 to 30, the inner sheet effectively conceals the respective intermediate segments of the first and second elastic members. Consequentially, it is difficult for the respective intermediate segments of the first and second elastic members to be visually recognized in the crotch region. Compared to the case in which the first and second elastic members have color different from that of the inner and outer sheets, the respective intermediate segments of the first and second elastic members are not highly visible and the article is more reliably protected from deterioration of its appearance.

In the article implemented so that the respective intermediate segments of the first and second elastic members have a stretch ratio in a range of 1.1 to 1.3, the liquid-absorbent layer has a sufficient stiffness to prevent the backsheet and the liquid-absorbent layer from contracting in the transverse direction even when the contractile force of the first and second elastic members acts upon the liquid-absorbent layer. Consequentially, it is difficult for the backsheet extending in the crotch region to be formed with wrinkles. Compared to the case in which the backsheet extending in the crotch region is formed with a plurality of irregular wrinkles, the article is more reliably protected from deterioration of its appearance.

In the article implemented so that the respective intermediate segments of the first and second elastic members are left free from the liquid-absorbent layer, it is not apprehended that the contractile force of the respective intermediate segments of the first and second elastic members might act directly upon the liquid-absorbent layer and cause the liquid-absorbent layer extending in the crotch region to be formed with the wrinkles as in the case in which the respective intermediate segments of the first and second elastic members are permanently bonded to the liquid-absorbent layer. It is also not apprehended that a liquid absorbing function of the liquid-absorbent layer might be deteriorated as in the case in which the liquid-absorbent layer is formed with a plurality of irregular wrinkles.

DETAILED DESCRIPTION OF THE PREFERRED EMBODIMENTS

Details of a disposable wearing article according to the present invention will be more fully understood from the description given hereunder with reference to the accompanying drawings.

Figure 1:
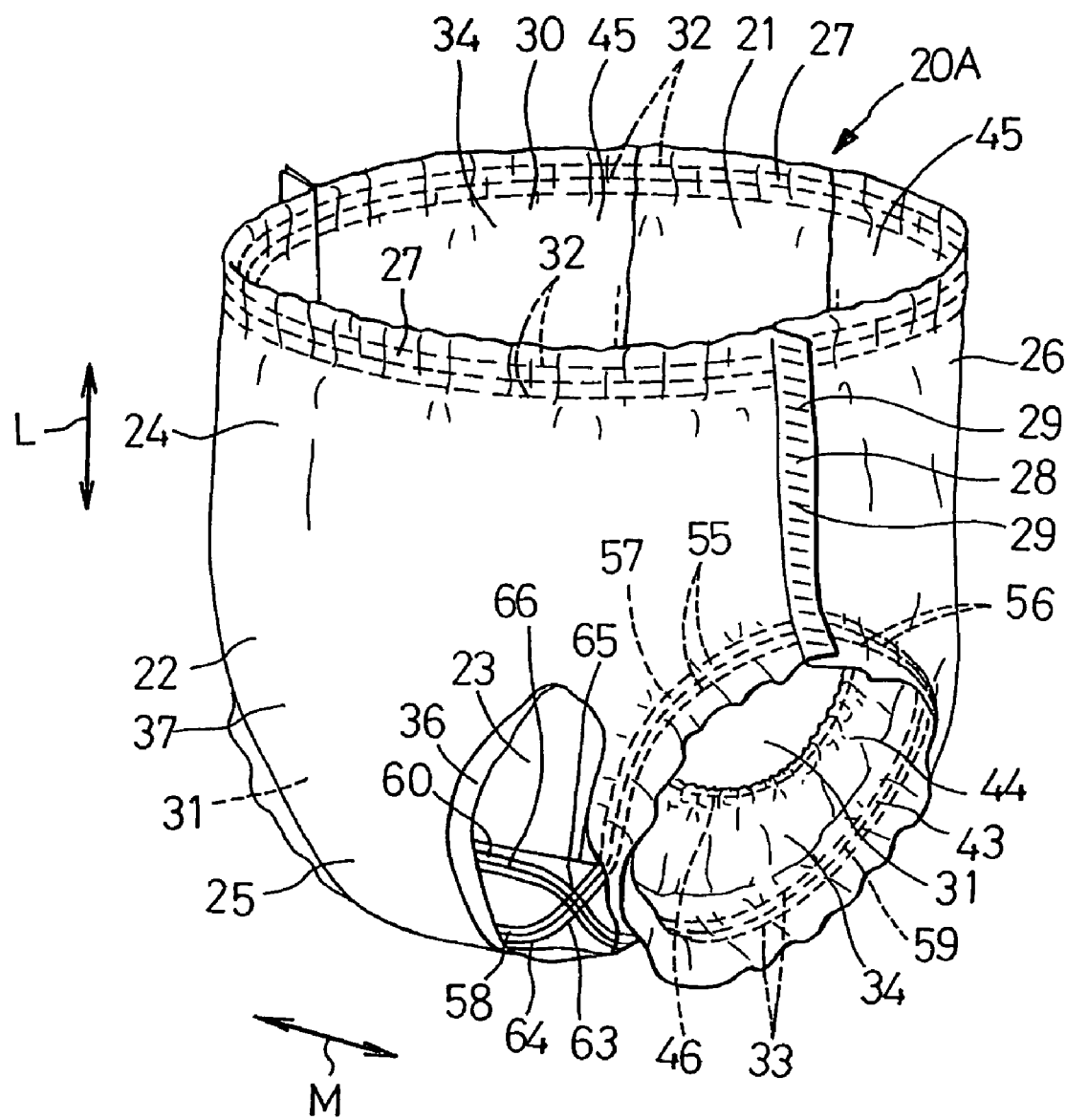
FIG. 1 is a partially cutaway perspective view showing a typical embodiment of the disposable wearing article according to the present invention.
Figure 2:
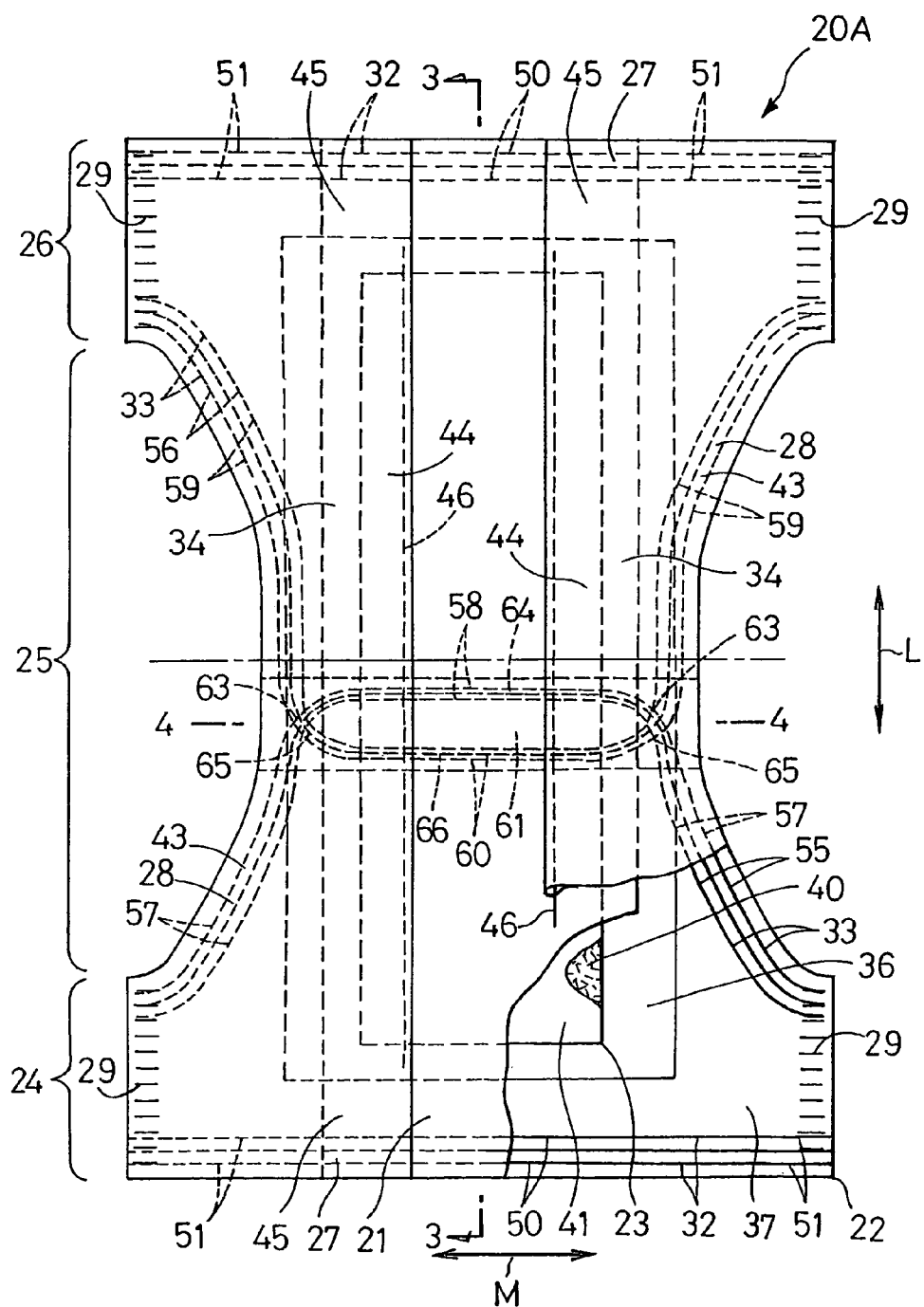
FIG. 2 is a partially cutaway developed plan view showing the article of FIG. 1.
Figure 3:
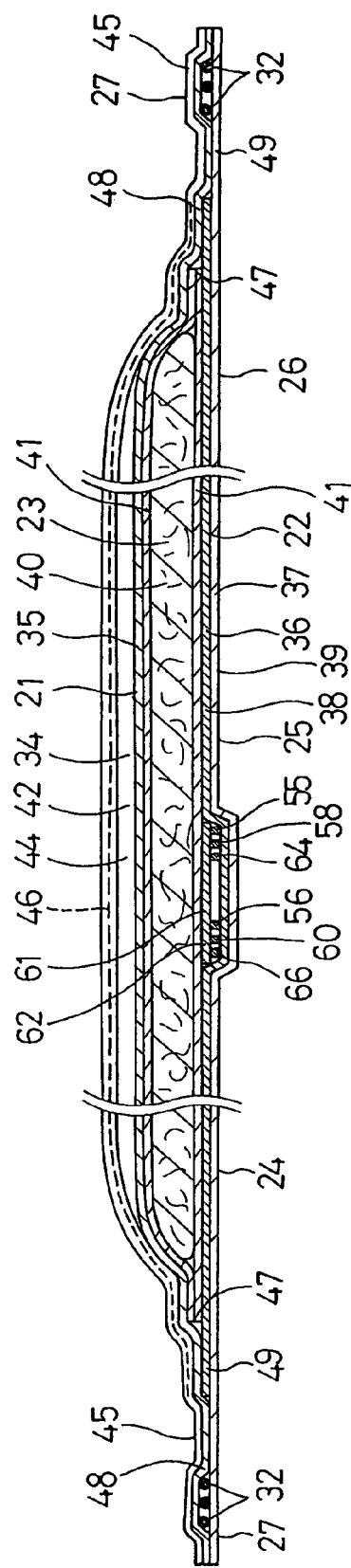
FIG. 3 is a sectional view taken along the line 3—3 in FIG. 2.
Figure 4:
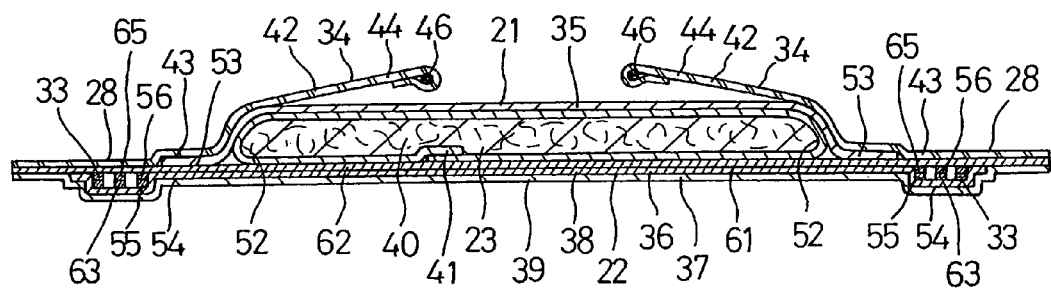
FIG. 4 is a sectional view taken along a line 4—4 in FIG. 2.

FIG. 1 is a partially cutaway perspective view showing disposable wearing article 20A as a typical embodiment of the present invention and FIG. 2 is a partially cutaway developed plan view showing the article 20A of FIG. 1 with front and rear waist regions 24, 26 disconnected from each other and FIG. 3 is a sectional view taken along a line 3—3 in FIG. 2 and FIG. 4 is a sectional view taken along a line 4—4 in FIG. 2. In FIGS. 1 and 2, a longitudinal direction is indicated by an arrow L and a transverse direction is indicated by an arrow M. Term "inner surfaces of top- and backsheets 21, 22 and leak-proof sheets 34" used herein refers to respective surfaces of these sheets facing a liquid-absorbent layer 23 and term "outer surfaces of these sheets 21, 22, 34" refers to respective surfaces of these sheets facing away from the liquid-absorbent layer 23.

The article 20A comprises the liquid-pervious topsheet 21 facing the wearer's skin, the liquid-impervious backsheet 22 facing away from the wearer's skin and the liquid-absorbent layer 23 interposed between these sheets 21, 22. The article 20A is configured to define the front and rear waist regions 24, 26 opposed to each other and a crotch region 25 extending between these waist regions 24, 26. The article 20A has longitudinally opposite ends 27 of the front and rear waist regions 24, 26, respectively, extending in the transverse direction and transversely opposite edges 28 of the front and rear waist regions 24, 26, respectively, extending in the longitudinal direction. The liquid-absorbent layer 23 extends between the front and rear waist regions 24, 26 except the longitudinally opposed ends 27 and the transversely opposite edges 28.

The article 20A has an hourglass-like planar shape wherein the transversely opposite edges 28 of the crotch region 25 describe circular arcs which are convex inward as viewed in the transverse direction, as will be seen in FIG. 2. In the article 20, the front and rear waist regions 24, 26 are put flat together along the transversely opposite edges 28 thereof and permanently bonded together at a plurality of heat-sealing lines 29 arranged intermittently along these opposite edges 28. As will be apparent from FIG. 1, the article 20A is of pants-type having a waist-hole 30 and a pair of leg-holes 31. The longitudinally opposite ends 27 of the article 20A are respectively provided with a plurality of waist elastic members 32 extending in the transverse direction and attached thereto in stretchable/contractible manner. The transversely opposite edges 28 of the crotch region 25 are respectively provided with a plurality of leg elastic members 33 extending in the longitudinal direction and attached thereto in a stretchable/contractible manner. The transversely opposite edges 28 are further provided with a pair of liquid-resistant leak-proof sheets 34 extending in the longitudinal direction from the front waist region 24 to the rear waist region 26.

The topsheet 21 is formed by hydrophilic fibrous nonwoven fabric 35 and its color is white or milky white. The backsheet 22 consists of inner sheet 36 facing the liquid-absorbent layer 23 and outer sheet 37 extending on the outer side of the inner sheet 36 between the front and rear waist regions 24, 26. The inner and outer sheets 36, 37 are put flat together and have mutually opposed surfaces bonded to each other by means of adhesive (not shown). Color of both the inner sheet 36 and the outer sheet 37 are white or milky white and color of the backsheet 22 consisting of these sheets 36, 37 is also white or milky white. The inner sheet 36 extends from the front waist region 24 to the rear waist region 26 except the longitudinally opposite ends 27 and the transversely opposite edges 26 so as to cover whole lower surface of the liquid-absorbent layer 23. The inner sheet 36 is formed by moisture-pervious but liquid-impervious non-stretchable plastic film 38 obtained by mono- or biaxial orientation of synthetic resin containing fine particles of inorganic substances such as calcium carbonate or barium sulfate. The outer sheet 37 is formed by hydrophobic fibrous nonwoven fabric 39.

The liquid-absorbent layer 23 comprises a liquid-absorbent core 40 and tissue paper 41 wrapping the core 40 in its entirety. The core 40 comprises a mixture of particular or fibrous super-absorbent polymer and fluff pulp or a mixture of particular or fibrous super-absorbent polymer, fluff pulp and thermoplastic synthetic resin fiber, in any case, compressed to a predetermined thickness. Consequentially, the liquid-absorbent layer 23 has stiffness higher than those of the top- and backsheets 21, 22. The liquid-absorbent layer 23 is bonded to respective inner surfaces of the top- and backsheets 21, 22 by the intermediary of tissue paper 41. The polymer may be selected from a group consisting of starch-based, cellulose-based and synthetic polymer.

The leak-proof sheets 34 are formed by hydrophobic fibrous nonwoven fabric 42. The respective leak-proof sheets 34 comprise fixed lateral sections 43 extending in the longitudinal direction along the respective edges 27 of the article 20A, free sections 44 extending in the longitudinal direction in parallel to the respective fixed sections 43 and normally biased to rise above the outer surface of the topsheet 21, longitudinally opposite fixed ends 45 lying on the longitudinally opposite ends 27 of the article 20A and collapsed inward as viewed in the transverse direction of the article 20A. Elastic members 46 extending in the longitudinal direction are attached to the free sections 44 in the vicinity of upper edges thereof in a stretchable/contractible manner. Specifically, these elastic members 46 are stretched at a predetermined ratio and permanently bonded in such stretched state to the free sections 44. In the leak-proof sheets 34, contractile force of the elastic members 46 causes the free sections 44 to contract and consequentially to rise above the outer surface of the topsheet 21. The free sections 44 form barriers serving to prevent bodily discharges from moving sideways.

The longitudinally opposite ends 27 are defined by respective ends 48, 49 of the top- and backsheets 21, 22 extending outward in the longitudinal direction beyond longitudinally opposite ends 47 of the liquid-absorbent layer 23 and the longitudinally opposite fixed ends 45 of the respective leak-proof sheets 34. Along the longitudinally opposite ends 27, the inner sheet 36 extends outward in the longitudinal direction beyond the ends 47 of the liquid-absorbent layer 23 and the topsheet 21 as well as the outer sheet 37 extend outward in the longitudinal direction beyond the inner sheet 36. Along the ends 27, the longitudinally opposite ends 48, 49 of the top- and backsheets 21, 22, respectively, and the longitudinally opposite fixed ends 45 of the respective leak-proof sheets 34 are put flat and bonded together. In each of the front and rear waist regions, the waist elastic members 32 have a transversely middle segment 50 interposed between the end 48 of the topsheet 21 and the end 49 of the backsheet 22 (the outer sheet 37) and permanently bonded to the respective inner surfaces of these sheets 21, 22, and transversely opposite ends 51 interposed between the end 49 of the backsheet 22 (the outer sheet 37) and the lateral sections 43 of the respective leak-proof sheets 34 and permanently bonded to the respective inner surfaces of these sheets 21, 34. Specifically, the elastic members 32 are stretched at a predetermined ratio and permanently bonded in such stretched state to these sheets 21, 22, 34.

The transversely opposite edges 28 of the article 20A are defined by transversely opposite edges 53, 54 of the top- and backsheets 21, 22, respectively, extending outward in the transverse direction beyond transversely opposite edges of the liquid-absorbent layer 23 and the fixed lateral sections 43 of the respective leak-proof sheets 34. Along the transversely opposite edges 28 of the article 20A, the topsheet 21 and the inner sheet 36 extend outward in the transverse direction slightly beyond the transversely opposite edges 52 of the liquid-absorbent layer 23. The leak-proof sheets 34 and the outer sheet 37 extend outward in the transverse direction beyond these sheets 21, 36. Along the transversely opposite edges 28 of the article 20A, the transversely opposite edges 53, 54 of the top- and backsheets 21, 22, respectively, and the lateral sections 43 of the respective leak-proof sheets 34 are put flat and bonded together.

The leg elastic members 33 comprise first elastic members 55 describing curves which extend from the side of the front waist region 24 so as to be convex toward a middle zone of the crotch region 25 and second elastic members 56 extending from the side of the rear waist region 26 so as to be convex toward the middle zone of the crotch region 25. More specifically, the first elastic members 55 describe substantially circular arcs which are convex toward the middle zone of the crotch region 25. The first elastic members 55 comprise transversely opposite lateral segments 57 extending in the longitudinal direction along the transversely opposite edges 28 of the article 20A and an intermediate segment 58 extending between these lateral segments 57 across the middle zone of the crotch region 25. The second elastic members 56 describe substantially circular arcs which are convex toward the middle zone of the crotch region 25. The second elastic members 56 comprise transversely opposite lateral segments 59 extending in the longitudinal direction along the transversely opposite edges 28 of the article 20A and an intermediate segment 60 extending between these lateral segments 59 across the middle zone of the crotch region 25. The lateral segments 57, 59 of these elastic members 55, 56, respectively, are interposed between the transversely opposite edges 54 of the backsheet 22 (the inner sheet 36 or the outer sheet 37) and the fixed lateral sections 43 of the respective leak-proof sheets 34 and permanently bonded to the respective inner surfaces of these sheets 22, 34 while these lateral segments 57, 59 are stretched at a predetermined ratio.

The respective intermediate segments 58, 60 of these elastic members 55, 56 are laid in the middle zone of the crotch region 25, more strictly, in zones located aside toward the front waist region 24. In a zone of the crotch region 25 including the intermediate segments 58, 60, there is provided a rectangular auxiliary sheet 61 being relatively long in the transverse direction to hold respective crossover sites 63, 65, as will be described later, of the intermediate segments 58, 60 against the inner sheet 36. As stock material for the auxiliary sheet 61, translucent non-stretchable plastic film 62 is used. The intermediate segments 58, 60 are sandwiched between the inner sheet 36 (the film 38) and the liquid-absorbent layer 23 through the intermediary of the auxiliary sheet 61. The intermediate segment 58 comprises the crossover sites 63 and a cross segment 64 extending in the transverse direction between the crossover sites 63. The intermediate segment 60 comprises crossover sites 65 and a cross segment 66 extending in the transverse direction between the crossover sites 65. The crossover sites 63, 65 intersect one with another immediately outside the transversely opposite edges 52 of the liquid-absorbent layer 23. These crossover sites 63, 65 are interposed between the inner sheet 36 and the auxiliary sheet 61 and permanently bonded to these sheets 36, 61 by means of adhesive (not shown). The cross segments 64, 66 are sandwiched between the inner sheet 36 and the auxiliary sheet 61 so as to extend across the liquid-absorbent layer 23. These cross segments 64, 66 are bonded neither to the inner sheet 36 nor the auxiliary sheet 61, i.e., left free from these sheets 36, 61. The auxiliary sheet 61 is sandwiched between the inner sheet 36 and the liquid-absorbent layer 23 (the tissue paper 41) so as to extend across the crotch region 25. The auxiliary sheet 61 is permanently bonded to the inner sheet 36 by means of adhesive (not shown) but not to the liquid-absorbent layer 23. Consequentially, the respective intermediate segments 58, 60 of the respective elastic members 55, 56 are left free from the liquid-absorbent layer 23. The crossover sites 63, 65 may be permanently bonded to the sheets 36, 61 with the intermediate segments 58, 60 being stretched in the transverse direction or substantially not stretched in the transverse direction.

The first and second elastic members 55, 56 are colored in white or milky white and such color is substantially same as those of the inner sheet 36 (the film 38) and the outer sheet 37 (the nonwoven fabric 39). Therefore, the backsheet 22 consisting of the inner and outer sheets 36, 37 effectively conceals the intermediate segments 58, 60 of these elastic members 55, 56.

While the inner and outer sheets 36, 37 as well as the first and second elastic members 55, 56 are normally colored in white or milky white, these sheets and elastic members may sometimes insensibly take on red, green, blue or yellow color. A color difference E1 of the first and second elastic members 55, 56 with respect to a standard white plate is in a range of 70 to 90 according to a following equation (1):

$$E1=\sqrt{(L0-L1)^2+(A0-A1)^2+(B0-B1)^2} \qquad \text{[EQUATION 1]}$$

where L1 represents a brightness of these elastic members 55, 56, L0 represents a standard of brightness, A1 represents a degree to which the elastic members 55, 56 take on red and green, A0 represents a degree to which the elastic members 55, 56 take on red and green, B1 represents a degree to which the elastic members take on blue and yellow and B0 represents a degree to which the elastic members 55, 56 take on blue and yellow. In this equation, L0 is 97.5, A0 is −0.35 and B0 is 0.25.

A color difference E2 of the inner sheet 36 with respect to the standard white plate is in a range of 85 to 115 according to a following equation (2):

$$E2=\sqrt{(L0-L2)^2+(A0-A2)^2+(B0-B2)^2} \qquad \text{[EQUATION 2]}$$

where L2 represents a brightness of the inner sheet 36, L0 represents the standard of brightness, A2 represents a degree to which the sheet 36 takes on red and green, A0 represents a degree to which the sheet 36 takes on red and green, B2 represents a degree to which the sheet 36 takes on blue and yellow and B0 represents a degree to which the sheet 36 takes on blue and yellow.

A color difference E3 of the outer sheet 37 with respect to the standard white plate is in a range of 85 to 115 according to a following equation (3):

$$E3=\sqrt{(L0-L3)^2+(A0-A3)^2+(B0-B3)^2} \qquad \text{[EQUATION 3]}$$

where L3 represents a brightness of the outer sheet 37, L0 represents the standard of brightness, A3 represents a degree to which the sheet 37 takes on red and green, A0 represents a degree to which the sheet 37 takes on red and green, B3 represents a degree to which the sheet 37 takes on blue and yellow and B0 represents a degree to which the sheet 37 takes on blue and yellow.

In the article 20A, the numeric value E2 of the inner sheet 36 is higher than the numeric value E1 of the elastic members 55, 56 and a color difference ΔE1 between the numeric value of E2 of the inner sheet 36 and the numeric value E1 of the elastic members 55, 56 is in a range of 10 to 30 according to a following equation (4):

$$\Delta E1=\sqrt{(L1-L2)^2+(A1-A2)^2+(B1-B2)^2} \qquad \text{[EQUATION 4]}$$

If this color difference ΔE1 is less than 10, the effect of the inner sheet 36 to conceal the elastic members 55, 56 will be insufficient and the color of the intermediate segments 58, 60 of the elastic members 55, 56 may be seen through the backsheet 22 from the outside. Particularly in the crotch region 25, these intermediate segments 58, 60 of the elastic members 55, 56 may jump to the eye and deteriorate appearance of the article 20A.

In the article 20A, it is preferred that the numeric value E3 of the outer sheet 37 is higher than the numeric value E1 of the elastic members 55, 56 and a color difference ΔE2 between the inner sheet 36 and the first and second elastic members 55, 56 obtained by a following equation (4):

$$\Delta E2=\sqrt{(L1-L3)^2+(A1-A3)^2+(B1-B3)^2} \qquad \text{[EQUATION 5]}$$

is in a range of 10 to 30. In addition, the numeric value E2 of the inner sheet 36 is preferably higher than the numeric value E3 of the outer sheet 37.

The respective brightness L1, L2, L3 of the sheets 36, 37 and the elastic members 55, 56, the degrees A1, A2, A3 to which the sheets 36, 37 and the elastic members 55, 56 take on red and green and the degrees B1, B2, B3 to which the sheets 36, 37 and the elastic members 55, 56 take on blue and yellow were measured using a calorimetric color difference meter ZE2000 (manufactured by Nippon Denshoku Industries Co., Ltd.) under the measuring condition as follow: measuring mode: reflection mode, measurement area: 30 mmØ.

Of the article 20A, a region in which the inner sheet 36 (the film 38) and the outer sheet 37 (the nonwoven fabric 39) constituting the backsheet 22 are placed upon each other presents a light transmission in a range of 20 to 50%. If the light transmission of this region in which the inner and outer sheets 36, 37 are placed upon each other exceeds 50%, the color of the intermediate segments 58, 60 of the elastic members 55, 56 will be easily transmitted through the backsheet 22 and therefore the intermediate segments 58, 60 will be easily seen through the backsheet 22 from the outside. Consequently, in the crotch region 25, these intermediate segments 58, 60 of the elastic members 55, 56 may jump to the eye and deteriorate appearance of the article 20A. The light transmission in the region in which the inner and outer sheets 36, 37 are placed upon each other was measured by a method as will be described below.

The region in which the inner and outer sheets 36, 37 constituting the backsheet 22 are placed upon each other was cut away from the article 20A to make a sample for measurement of light transmission. Measurement of light transmission was conducted on this sample. For this measurement of light transmission, the turbidity meter NDH300A (manufactured by Nippon Denshoku Industries Co., Ltd.) was used. The measuring condition: measurement was conducted using the photoelectric photometer of integrating sphere type over an area of 12 mmØ in pursuance to the standard JIS K 7105.

In the article 20A, the intermediate segments 58, 60 of the elastic members 55, 56 are stretched at a ratio in a range of 1.1 to 1.3 and a stretch stress of the intermediate segments 58, 60 is lower than that of the lateral segments 57, 59. If the stretch ratio of the intermediate segments 58, 60 exceeds 1.3, a contractile force of the intermediate segments 58, 60 of the first and second elastic members 55, 56 will cause the backsheet 22 as well as the liquid-absorbent layer 23 to contract in the transverse direction. As a result, the backsheet 22 as well as the liquid-absorbent layer 23 in the crotch region 25 will form a plurality of irregular wrinkles. These wrinkles on the backsheet 22 formed due to the contractile force of the intermediate segments 58, 60 will be highly visible and deteriorate the appearance of the article 20A. The stretch ratio of the intermediate segments 58, 60 was measured by a method as will be described below.

(1) Middle regions (each including the sheets 21, 22, 61 and the intermediate segments 58, 60 of the elastic members 55, 56) of the respective crotch regions 25 were cut away from the five articles 20A to make five samples for measurement of the stretch ratio. In the respective samples, the crossover sites 63, 65 of the intermediate segments 58, 60 were marked. Following the track of the intermediate segments 58, 60 of the elastic members 55, 56, the length of the intermediate segments 58, 60 was measured for each of the samples by use of measuring tape. From measuring result for five samples, an average length value Z1 was calculated.

(2) Then, toluene was used to dissolve the adhesive and thereby to separate the sheets 21, 22, 61 and the elastic members 55, 56 one from another. A length of the intermediate segments 58, 60 of the elastic members 55, 56 left free from the other components was measured using the measuring tape for each of the samples and an average length value Z2 was calculated. A stretch ratio was obtained by calculating Z1·Z2. The stretch ratio obtained for the samples was adopted as the stretch ratio of the article 20A along the intermediate segments 58, 60.

In the article 20A, the liquid-absorbent layer 23 has a bending resistance in a range of 0.08 to 0.15 N·cm. If the bending resistance of the liquid-absorbent layer 23 is less than 0.08 N·cm, a contractile force of the intermediate segments 58, 60 will cause the liquid-absorbent layer 23 to contract in the transverse direction and thereby cause the backsheet 22 as well as the liquid-absorbent layer 23 to be formed with a plurality of irregular wrinkles being highly visible and deteriorating the appearance of the article 20A. In addition, the liquid-absorbent layer 23 will have a liquid-absorbing function deteriorated. If the bending resistance of the liquid-absorbent layer 23 exceeds 0.15 N·cm, the liquid-absorbent layer 23 will have a flexibility deteriorated and the liquid-absorbent layer 23 may uncomfortably stimulate the wearer's skin. Consequently, a feeling to wear the article 20A will be deteriorated. The bending resistance of the liquid-absorbent layer 23 was measured by Taber's method (pursuant to JIS P 8125). Details of the bending resistance measuring method will be described later.

(1) The liquid-absorbent layer was cut into samples for measurement of the bending resistance each dimensioned to be 70 mm in the longitudinal direction·38.1 mm in the transverse direction. To measure the bending resistance, a thickness gauge (PEACOCK DIAL THICKNESS GAUGE No. C11352: diameter of 50 mm·load of 3 g/cm$^2$) and Taber's Stiffness Tester (Taber's Tester) manufactured by YASUDA-SEIKI-SEISAKUSHO, LTD. were used.

(2) The bending resistance is measured in steps as follow: (a) Thickness dimension W of the sample is measured by the thickness gauge. (b) The sample is introduced into a nip between paired rollers of a sample bending mechanism and attached thereto so that a sample chuck is aligned with the sample in the same straight line and a center pitch line is aligned with 0 of a load scale (the chuck clearance is adjusted to the thickness of the sample). (c) A sum of right and left gaps between the rollers and the sample is adjusted to W·0.80 (mm) and a distance from the rollers to the sample is adjusted to about 0.5 mm. (d) The sample bending mechanism is clockwise rotated until a pitch line of the sample bending mechanism indicating 15° falls into line with a pointer of a load pendulum whereupon rotation of the bending mechanism is stopped. A numeric value X on the load scale indicated at this moment by the pointer of the pendulum is read off. (e) Herewith, the sample bending mechanism is counterclockwise rotated until the pitch line of the sample bending mechanism indicating 15° falls into line with the pointer of the load pendulum whereupon rotation of the bending mechanism is stopped. A numeric value Y on the load scale indicated at this moment by the pointer of the pendulum is read off. An auxiliary weight is appropriately selected so that the load scale value may fall within a range of 15 to 85% of full scale value and the selected auxiliary weight is attached to the sample.

(3) The numeric values X, Y on the load scale having been read off immediately after clockwise rotation and counterclockwise rotation are used to obtain a bending resistance of the sample from an equation as follows: Bending resistance (N·cm)={(X+Y)/2}·{(numeric value associated with auxiliary weight)/1000·9.807}. The bending resistance of the sample calculated in this manner was adopted as the bending resistance of the liquid-absorbent layer 23 in this article 20A.

The light transmission of the article 20A in the region in which the inner and outer sheets 36, 37 constituting the backsheet 22 are placed upon each other is in a range of 20 to 50% and the intermediate segments 58, 60 of the first and second elastic members 55, 56 are sandwiched between the liquid-absorbent layer 23 and the inner sheet 36. Such arrangement makes it difficult for the color of the respective intermediate segments 58, 60 of the elastic members 55, 56 to be transmitted through the backsheet 22 and thereby to be seen through the backsheet 22 from the outside. In the article 20A, the color of the first and second elastic members 55, 56 is substantially same as the color of the inner and outer sheets 36, 37 and therefore the backsheet 22 comprising the inner and outer sheets 36, 37 effectively conceals the respective intermediate segments 58, 60 of the elastic members 55, 56. Compared to the case in which the color of the first and second elastic members are different from the color of the inner and outer sheets 36, 37, the article 20A ensures that the respective intermediate segments 58, 60 of the elastic members 55, 56 are not visually recognized from the outside of the backsheet 22. The article 20A is characterized also in that the numeric value E2 of the inner sheet 36 is higher than the numeric value E1 of the elastic members 55, 56 and the color difference ΔE1 between the inner sheet 36 and the elastic members 55, 56 is in a range of 10 to 30. Consequently, the effect of the inner sheet 36 to conceal the elastic members 55, 56 is substantially higher than in the case in which the color difference ΔE1 is less than 10. Specifically, it is difficult to recognize visually the respective intermediate segments 58, 60 of these elastic members 55, 56 from the outside of the backsheet 22. The article 20A is further characterized in that the stretch ratio of the respective intermediate segments 58, 60 of the elastic members 55, 56 is in a range of 1.1 to 1.3 and therefore there is no anxiety that the backsheet 22 as well as the liquid-absorbent layer 23 might contract in the transverse direction and form the wrinkles even if the contractile force of the first and second elastic members 55, 56 act upon the liquid-absorbent layer 23. This is for the reason that the liquid-absorbent layer 23 has a sufficient stiffness to prevent such wrinkles from being formed. In the article 20A, the respective intermediate segments 58, 60 of the elastic members 55, 56 are not highly visible and free from the apprehension that the backsheet 22 in the crotch region 25 might form the wrinkles. Compared to the case in which the respective intermediate segments 58, 60 of the elastic members 55, 56 are highly visible and/or the backsheet 22 forms a plurality of irregular wrinkles, the article 20A is ensured to keep its good appearance.

In the article 20A, the respective intermediate segments 58, 60 of the first and second elastic members 55, 56 are not bonded to the liquid-absorbent layer 23, i.e., left from the liquid-absorbent layer 23 so that the contractile force of the respective intermediate segments 58, 60 of the elastic members 55, 56 do not act directly upon the liquid-absorbent layer 23. Consequentially, the liquid-absorbent layer 23 in the crotch region 25 is sufficiently resistant to formation of the wrinkles even when the intermediate segments 58, 60 contract. Compared to the case in which the liquid-absorbent layer 23 in the crotch region 25 is formed with a plurality of irregular wrinkles, it is ensured for this article 20A to prevent a liquid-absorbing function of the liquid-absorbent layer 23 from being deteriorated. Bodily waste discharged on the article 20A put on the wearer's body is absorbed by the liquid-absorbent layer 23 through the topsheet 21 and retained therein.

Figure 5:
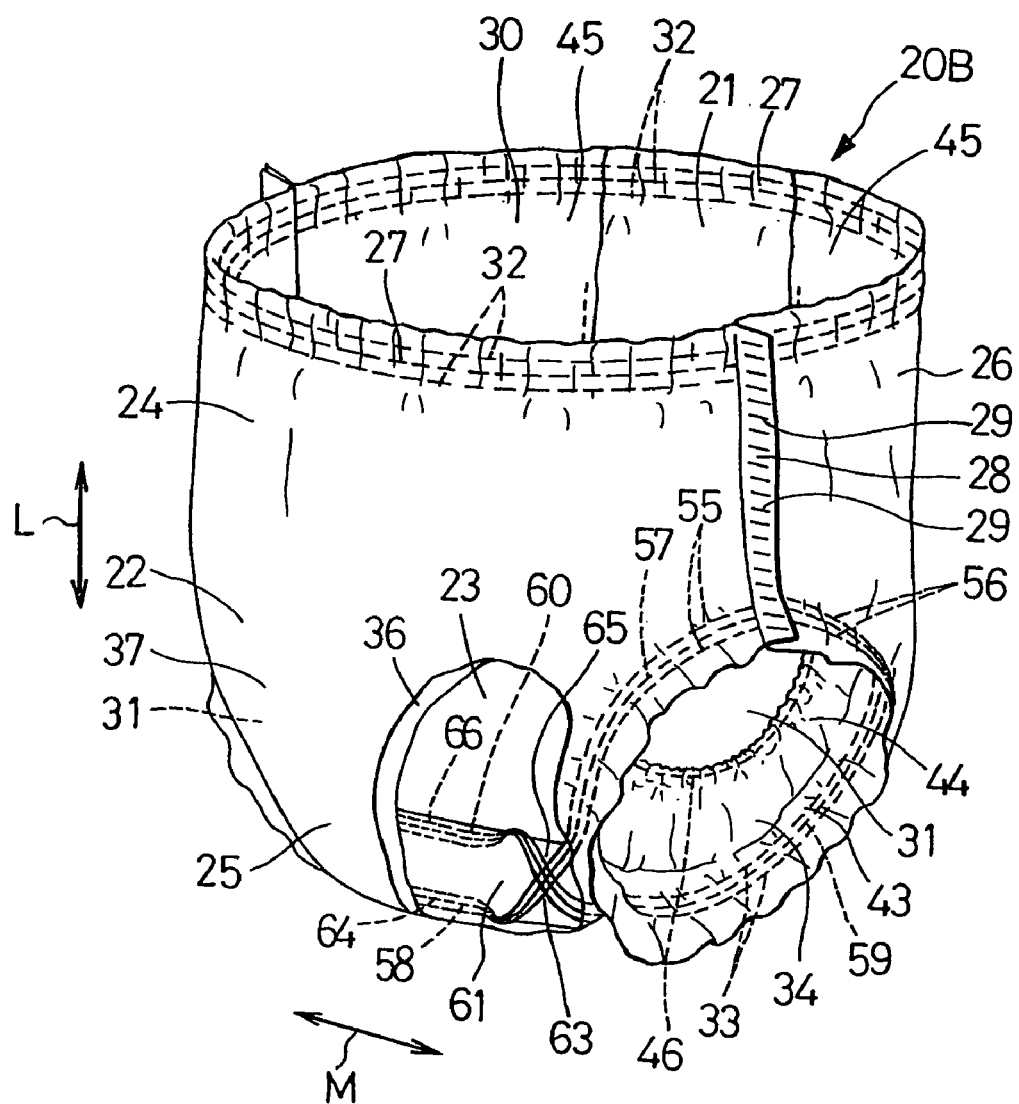
FIG. 5 is a partially cutaway perspective view showing one preferred embodiment of the wearing article according to the present invention.
Figure 6:
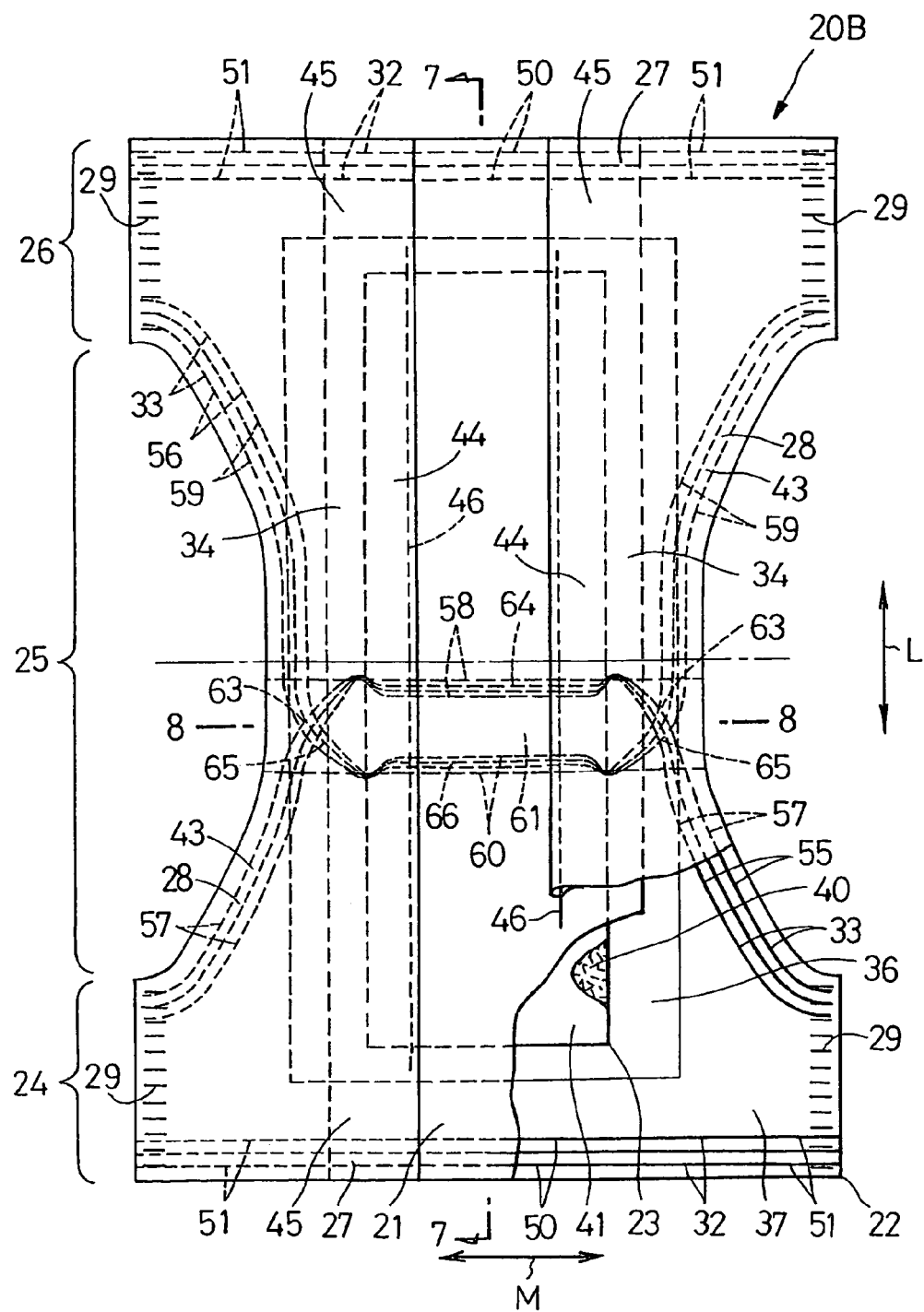
FIG. 6 is a partially cutaway developed plan view showing the article of FIG. 5.
Figure 7:
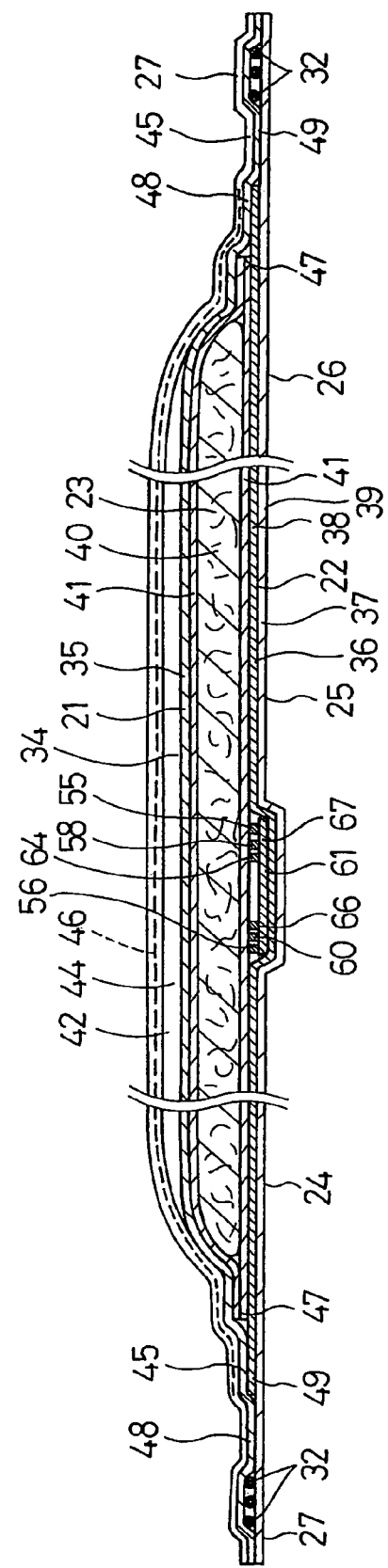
FIG. 7 is a sectional view taken along the line 7—7 in FIG. 6.
Figure 8:
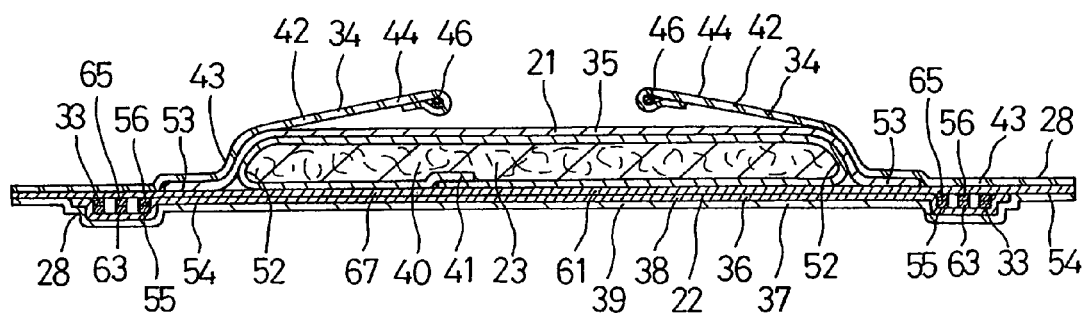
FIG. 8 is a sectional view taken along the line 8—8 in FIG. 6.

FIG. 5 is a perspective view showing a wearing article 20B as one preferred embodiment according to the present invention as partially broken away and FIG. 6 is a partially cutaway developed plan view showing the article 20B of FIG. 5 with the front and rear waist regions 24, 25 disconnected from each other. FIG. 7 is a sectional view taken along a line 7—7 in FIG. 6 and FIG. 8 is a sectional view taken along a line 8—8 in FIG. 6. In FIGS. 5 and 6 also, a longitudinal direction is indicated by an arrow L and a transverse direction is indicated by an arrow M. This article 20B is distinguished from the article 20A of FIG. 1 in that the respective cross segments 64, 66 of the elastic members 55, 56 are sandwiched between the liquid-absorbent layer 23 and the auxiliary sheet 61 and the auxiliary sheet 61 has the substantially same color as those of the inner and outer sheets 36, 37 and the elastic members 55, 56. The other features are common to the article 20A of FIG. 1, so the components of the article 20B similar to those of the article 20A are merely designated by the similar reference numerals and detailed description thereof will be omitted hereunder.

The article 20B is of pants-type having the waist-hole 30 and the leg-holes 31 and comprises the liquid-pervious topsheet 21, the liquid-impervious backsheet 22 and the liquid-absorbent layer 23 sandwiched between these sheets 21, 22. The article 20B is configured to define the front and rear waist regions 24, 26, the crotch region 25, the longitudinally opposite ends 27 and the transversely opposite edges 28. The longitudinally opposite ends 27 are respectively provided with a plurality of waist elastic members 32 bonded thereto in a stretchable/contractible manner. The transversely opposite edges 28 of the crotch region 25 are respectively provided with a plurality of leg elastic members 33 bonded thereto in a stretchable/contractible manner. The transversely opposite edges 28 are further provided with a pair of liquid-resistant leak-proof sheets 34 extending in the longitudinal direction from the front waist region 24 to the rear waist region 26.

The topsheet 21 is formed by hydrophilic fibrous nonwoven fabric 35 and its color is white or milky white. The backsheet 22 consists of inner sheet 36 facing the liquid-absorbent layer 23 and outer sheet 37 extending on the outer side of the inner sheet 36. Color of both the inner sheet 36 and the outer sheet 37 are white or milky white and color of the backsheet 22 consisting of these sheets 36, 37 is also white or milky white. The inner sheet 36 extends from the front waist region 24 to the rear waist region 26 except the longitudinally opposite ends 27 and the transversely opposite edges 26 so as to cover whole lower surface of the liquid-absorbent layer 23. The inner sheet 36 is formed by moisture-pervious but liquid-impervious non-stretchable plastic film 38 obtained by mono- or biaxial orientation of synthetic resin containing fine particles of inorganic substances such as calcium carbonate or barium sulfate. The outer sheet 37 is formed by hydrophobic fibrous nonwoven fabric 39. The liquid-absorbent layer 23 comprises a liquid-absorbent core 40 and tissue paper 41 wrapping the core 40 in its entirety. The liquid-absorbent layer 23 is bonded to respective inner surfaces of the top- and backsheets 21, 22.

The leak-proof sheets 34 are formed by hydrophobic fibrous nonwoven fabric 42. The respective leak-proof sheets 34 comprise the fixed lateral sections 43 extending in the longitudinal direction along the respective edges 27 of the article 20A, the free sections 44 extending in the longitudinal direction in parallel to the respective fixed sections 34 and normally biased to rise above the outer surface of the topsheet 21 and the longitudinally opposite fixed ends 45 collapsed inward as viewed in the transverse direction of the article 20B. The elastic members 46 extending in the longitudinal direction are attached to the free sections 44 in the vicinity of upper edges thereof in a stretchable/contractible manner. Specifically, these elastic members 46 are stretched at a predetermined ratio and permanently bonded in such stretched state to the free sections 44. In the leak-proof sheets 34, contractile force of the elastic members 46 causes the free sections 44 to contract and consequentially to rise above the outer surface of the topsheet 21. The free sections 44 form barriers serving to prevent bodily discharges from moving sideways.

The longitudinally opposite ends 27 are defined by respective ends 48, 49 of the top- and backsheets 21, 22 and the longitudinally opposite fixed ends 45 of the respective leak-proof sheets 34. Along the longitudinally opposite ends 27, the respective ends 45, 48, 49 of these sheets 21, 22, 34 are put flat and bonded together. The waist elastic members 32 have the transversely middle segments 50 permanently bonded to the inner surfaces of the sheets 21, 22 and the transversely opposite ends 51 permanently bonded to the inner surfaces of the sheets 23, 34. The transversely opposite edges 28 of the article 20B are defined by the transversely opposite edges 53, 54 of the top- and backsheets 21, 22, respectively, and the fixed lateral sections 43 of the respective leak-proof sheets 34. Along the transversely opposite edges 28 of the article 20B, the transversely opposite edges 43, 53, 54 of these sheets 21, 22, 34, are put flat and bonded together.

The leg elastic members 33 comprise the first elastic members 55 describing curves which extend from the side of the front waist region 24 so as to be convex toward the middle zone of the crotch region 25 and second elastic members 56 extending from the side of the rear waist region 26 so as to be convex toward the middle zone of the crotch region 25. More specifically, the first elastic members 55 comprise the transversely opposite lateral segments 57 extending along the transversely opposite edges 28 of the article 20B and an intermediate segment 58 extending between these lateral segments 57 across the middle zone of the crotch region 25. The second elastic members 56 comprise the transversely opposite lateral segments 59 extending along the transversely opposite edges 28 of the article 20B and an intermediate segment 60 extending across the middle zone of the crotch region 25. The lateral segments 57, 59 of these elastic members 55, 56, respectively, are interposed between the transversely opposite edges 54 of the backsheet 22 (the inner sheet 36 or the outer sheet 37) and the fixed lateral sections 43 of the respective leak-proof sheets 34 and permanently bonded to the respective inner surfaces of these sheets 22, 34 while these lateral segments 57, 59 are stretched at a predetermined ratio.

The respective intermediate segments 58, 60 of these elastic members 55, 56 are laid in the middle zone of the crotch region 25, more strictly, in the zones located aside toward the front waist region 24. In a zone of the crotch region 25 including the intermediate segments 58, 60, there is provided the rectangular auxiliary sheet 61 being relatively long in the transverse direction to hold respective crossover sites 63, 65 of the intermediate segments 58, 60 against the inner sheet 36. The intermediate segments 58, 60 are sandwiched between the inner sheet 36 (the film 38) and the liquid-absorbent layer 23 through the intermediary of the auxiliary sheet 61. The intermediate segment 58 comprises the crossover sites 63 and the cross segment 64 extending in the transverse direction between these crossover sites 63. The intermediate segment 60 comprises crossover sites 65 and the cross segment 66 extending in the transverse direction between the crossover sites 65. These crossover sites 63, 65 intersect one with another immediately outside the transversely opposite edges 52 of the liquid-absorbent layer 23. These crossover sites 63, 65 are interposed between the inner sheet 36 and the auxiliary sheet 61 and permanently bonded to these sheets 36, 61 by means of adhesive (not shown). The cross segments 64, 66 are sandwiched between the liquid-absorbent layer 23 and the auxiliary sheet 61 so as to extend across the liquid-absorbent layer 23. These cross segments 64, 66 are bonded neither to the liquid-absorbent layer 23 (the tissue paper 41) nor the auxiliary sheet 61, i.e., left free from these layer and sheet 23, 61.

The auxiliary sheet 61 is sandwiched between the liquid-absorbent layer 23 (the tissue paper 41) and the inner sheet 36 so as to extend across the crotch region 25. The auxiliary sheet 61 is permanently bonded to the inner sheet 36 by means of adhesive (not shown) but not to the liquid-absorbent layer 23. Consequentially, the respective intermediate segments 58, 60 of the respective elastic members 55, 56 are left free from the liquid-absorbent layer 23. The crossover sites 63, 65 may be permanently bonded to the sheets 36, 61 with the intermediate segments 58, 60 being stretched in the transverse direction or substantially not stretched in the transverse direction. The auxiliary sheet 61 is formed by moisture-pervious but liquid-impervious non-stretchable plastic film 38 obtained by mono- or biaxial orientation of synthetic resin containing fine particles of inorganic substances such as calcium carbonate or barium sulfate. Color of the auxiliary sheet 61 is white or milky white and substantially same as the color of the sheets 36, 37 and the elastic members 55, 56.

The first and second elastic members 55, 56 are colored in white or milky white and such color is substantially same as those of the inner sheet 36 (the film 38), the outer sheet 37 (the nonwoven fabric 39) and the auxiliary sheet 61 (the film 67). Therefore, the backsheet 22 and the auxiliary sheet 61 effectively conceal the intermediate segments 58, 60 of these elastic members 55, 56. It should be noted here that the region concealed by the auxiliary sheet 61 is limited to the respective cross segments 64, 66 of the intermediate segments except the crossover sites 63, 65.

Similarly to the case of the article 20A, in the article 20B also, the numeric value E2 of the inner sheet 36 is higher than the numeric value E1 of the elastic members 55, 56 and a color difference $\Delta E2$ between the inner sheet 36 and the first and second elastic members 55, 56 is in range of 10 to 30. The color difference $\Delta E2$ between the outer sheet 37 and the first and second elastic members 55, 56 is preferably in a range of 10 to 30. The numeric value E2 of the inner sheet 36 is preferably higher than the numeric value E3 of the outer sheet 37. If the color difference $\Delta E1$ between the inner sheet 36 and the elastic members 55, 56 is less than 10, the effect of the inner sheet 36 to conceal the elastic members 55, 56 will be insufficient and the color of the intermediate segments 58, 60 of the elastic members 55, 56 may be seen through the backsheet 22 from the outside. Particularly in the crotch region 25, these intermediate segments 58, 60 of the elastic members 55, 56 may jump to the eye and deteriorate appearance of the article 20B. The numeric values E1, E2, E3 and the color differences $\Delta E1$, $\Delta E2$ between the elastic members 55, 56 and the inner and outer sheets 36, 37, respectively, can be calculated by the same methods as those having been described with respect to the article 20A of FIG. 1.

Of the article 20B, the region in which the inner and outer sheets 36, 37 are placed upon each other presents a light transmission in a range of 20 to 50%. If the light transmission of this region in which the inner and outer sheets 36, 37 are placed upon each other exceeds 50%, the color of the intermediate segments 58, 60 of the elastic members 55, 56 will be easily transmitted through the backsheet 22 and therefore the intermediate segments 58, 60 will be easily seen through the backsheet 22 from the outside. Consequently, in the crotch region 25, these intermediate segments 58, 60 of the elastic members 55, 56 may jump to the eye and deteriorate appearance of the article 20A. The light transmission in the region in which the inner and outer sheets 36, 37 are placed upon each other can be measured by the same method as the method having been described with respect to the article 20A of FIG. 1.

In the article 20B, the intermediate segments 58, 60 of the elastic members 55, 56 are stretched at a ratio in a range of 1.1 to 1.3 and a stretch stress of the intermediate segments 58, 60 is lower than that of the lateral segments 57, 59. If the stretch ratio of the intermediate segments 58, 60 exceeds 1.3, a contractile force of the intermediate segments 58, 60 of the first and second elastic members 55, 56 will cause the backsheet 22 as well as the liquid-absorbent layer 23 to contract in the transverse direction. As a result, the backsheet 22 as well as the liquid-absorbent layer 23 in the crotch region 25 will form a plurality of irregular wrinkles. These wrinkles on the backsheet 22 formed due to the contractile force of the intermediate segments 58, 60 will be highly visible and deteriorate the appearance of the article 20B. The stretch ratio of the intermediate segments 58, 60 can be measured by the same method as the method having been described with respect to the article 20A of FIG. 1.

In the article 20B, the liquid-absorbent layer 23 has a bending resistance in a range of 0.08 to 0.15 N·cm. If the bending resistance of the liquid-absorbent layer 23 is less than 0.08 N·cm, a contractile force of the intermediate segments 58, 60 will cause the liquid-absorbent layer 23 to contract in the transverse direction and thereby cause the backsheet 22 as well as the liquid-absorbent layer 23 to be formed with a plurality of irregular wrinkles being highly visible and deteriorating the appearance of the article 20B. In addition, the liquid-absorbent layer 23 will have a liquid-absorbing function deteriorated. If the bending resistance of the liquid-absorbent layer 23 exceeds 0.15 N·cm, the liquid-absorbent layer 23 will have a flexibility deteriorated and the liquid-absorbent layer 23 may uncomfortably stimulate the wearer's skin. Consequently, a feeling to wear the article 20B will be deteriorated. The bending resistance of the liquid-absorbent layer 23 can be measured by the same method as the method having been described with respect to the article 20A of FIG. 1.

The light transmission of the article 20B in the region in which the inner and outer sheets 36, 37 constituting the backsheet 22 are placed upon each other is in a range of 20 to 50% and the intermediate segments 58, 60 of the first and second elastic members 55, 56 are sandwiched between the liquid-absorbent layer 23 and the inner sheet 36. Such arrangement makes it difficult for the color of the respective intermediate segments 58, 60 of the elastic members 55, 56 to be transmitted through the backsheet 22 and thereby to be seen through the backsheet 22 from the outside. In the article 20B, the color of the first and second elastic members 55, 56 is substantially same as the color of the inner sheet 36, the outer sheets 37 and the auxiliary sheet 61. Consequentially, the backsheet 22 and the auxiliary sheet 61 effectively conceal the respective intermediate segments 58, 60 of the elastic members 55, 56. Compared to the case in which the color of the first and second elastic members are different from the color of the inner and outer sheets 36, 37, the article 20B ensures that the respective intermediate segments 58, 60 of the elastic members 55, 56 are not visually recognized from the outside of the backsheet 22. The article 20B is characterized also in that the color difference ΔE1 between the inner sheet 36 and the elastic members 55, 56 is in a range of 10 to 30. Consequently, the effect of the inner sheet 36 to conceal the elastic members 55, 56 is substantially higher than in the case in which the color difference ΔE1 is less than 10. Specifically, it is difficult to recognize visually the respective intermediate segments 58, 60 of these elastic members 55, 56 from the outside of the backsheet 22. The article 20B is further characterized in that the stretch ratio of the respective intermediate segments 58, 60 of the elastic members 55, 56 is in a range of 1.1 to 1.3 and therefore there is no anxiety that the backsheet 22 as well as the liquid-absorbent layer 23 might contract in the transverse direction and form the wrinkles even if the contractile force of the first and second elastic members 55, 56 act upon the liquid-absorbent layer 23. This is for the reason that the liquid-absorbent layer 23 has a sufficient stiffness to prevent formation of such wrinkles. In the article 20B, the respective intermediate segments 58, 60 of the elastic members 55, 56 are not highly visible and free from the apprehension that the backsheet 22 in the crotch region 25 might form the wrinkles. Compared to the case in which the respective intermediate segments 58, 60 of the elastic members 55, 56 are highly visible and/or the backsheet 22 forms a plurality of irregular wrinkles, the article 20B is ensured to keep its goof appearance.

In the article 20B, the respective intermediate segments 58, 60 of the first and second elastic members 55, 56 are not bonded to the liquid-absorbent layer 23, i.e., left from the liquid-absorbent layer 23 so that the contractile force of the respective intermediate segments 58, 60 of the elastic members 55, 56 do not act directly upon the liquid-absorbent layer 23. Consequentially, the liquid-absorbent layer 23 in the crotch region 25 is sufficiently resistant to formation of the wrinkles even when the intermediate segments 58, 60 contract. Compared to the case in which the liquid-absorbent layer 23 in the crotch region 25 is formed with a plurality of irregular wrinkles, it is ensured for this article 20B to prevent a liquid-absorbing function of the liquid-absorbent layer 23 from being deteriorated.

As stock material for the topsheet 21, it is also possible to use, in addition to the hydrophilic fibrous nonwoven fabric 35, hydrophobic fibrous nonwoven fabric having a plurality of apertures. As stock material for the inner sheet 35 and the auxiliary sheet 61, it is also possible to use hydrophobic fibrous nonwoven fabric. As stock material for the leak-proof sheets 34 and the outer sheet 37, it is also possible to use breathable but liquid-impervious plastic film. As stock material for the leak-proof sheets 34, the inner and outer sheets 36, 37 and the auxiliary sheet 61, it is also possible to use a composite sheet consisting of breathable but liquid-impervious plastic film and hydrophobic fibrous nonwoven fabric laminated with each other. As stock material for the leak-proof sheets 34, the inner and outer sheets 36, 37 and the auxiliary sheet 61, it is also possible to use composite nonwoven fabric (SM nonwoven fabric) consisting of spun bond fibrous nonwoven fabric having high strength as well as good flexibility and laminated on one surface of melt blown fibrous nonwoven fabric having a high water resistance or composite nonwoven fabric (SMS nonwoven fabric) consisting of the spun bond fibrous nonwoven fabric laminated on both surfaces of the melt blown fibrous nonwoven fabric. As stock material for the elastic members 32, 33, 46, it is possible to use thread-like natural or synthetic rubber.

The fibrous nonwoven fabric may be selected from a group consisting of t spun lace nonwoven fabric, needle punch nonwoven fabric, melt blown nonwoven fabric, thermal bond nonwoven fabric, spun bond nonwoven fabric and chemical bond nonwoven fabric. The hydrophilic fibrous nonwoven fabric may be made of any one of synthetic fiber modified to become hydrophilic, semi-synthetic fiber and regenerated fiber, or composite fiber consisting of a mixture thereof. The hydrophobic fibrous nonwoven fabric may contain therein water repellent treated semi-synthetic fiber or regenerated fiber. While not specified, the synthetic fiber may be selected from a group consisting of polyester-, polyacrylonitrile-, polyvinylchloride-, polyethylene-, polypropylene- and polystyrene-based synthetic fibers. It is also possible touse, as synthetic fiber, core-sheath-type composite fiber, parallel-type composite fiber, modified macaroni fiber, micro-porous fiber or conjugative type composite fiber.

Bonding of the sheets 21, 22, 34 one to another, bonding of the liquid-absorbent layer 23 to the sheets 21,22, bonding of the elastic members 32, 33, 46 to the sheets 21, 22, 34 may be carried out using adhesive. The sheets 21, 22, 34 may be coated with adhesive preferably in the pattern such as spiral, wavy, zigzag, dotted or striped pattern. By coating the sheets 21, 22, 34 with adhesive in such patter, these sheets 21, 22, 23 are intermittently bonded one to another, the liquid-absorbent layer 23 is intermittently bonded to the sheets 21, 22 and the elastic members 32, 33, 46 are intermittently bonded to the sheets 21, 22, 34. Adhesive may be selected from a group consisting of hot melt adhesive, acrylic adhesive and rubber-based adhesive.

The entire discloses of Japanese Patent Application No. 2005-12079 filed on Jan. 19, 2005 including specification, drawings and abstract are herein incorporated by reference in its entirety.

What is claimed is:

1. A disposable wearing article, comprising:
a topsheet adapted to face a wearer's skin;
a backsheet adapted to face away from the wearer's skin;
a liquid-absorbent layer sandwiched between said topsheet and backsheet;
a front waist region;
a rear waist region;
a crotch region extending in a longitudinal direction of the article between said waist regions;
longitudinally opposite ends extending in a transverse direction of the article and transversely opposite edges extending in the longitudinal direction;
leg elastic members attached to the transversely opposite edges in a stretchable/contractible manner, said leg elastic members comprising:
first elastic members extending from said front waist region into said crotch region so as to define a first curve convex toward said rear waist region, and
second elastic members extending from said rear waist region into said crotch region so as to define a second curve convex toward the front waist region, and
each of said first and second elastic members having opposite lateral segments and an intermediate segment extending between said lateral segments across said liquid-absorbent layer;
said backsheet comprising:
an inner sheet facing said liquid-absorbent layer and extending in at least said crotch region, and
an outer sheet on an outside of said inner sheet and extending between said front and rear waist regions,
a region of said backsheet in which said inner and outer sheets are placed upon each other having a light transmission in a range of 20 to 50%, and
the respective intermediate segments of said first and second elastic members being sandwiched between said liquid-absorbent layer and said inner sheet; and
a non-stretchable auxiliary sheet sandwiched between the inner sheet and the liquid-absorbent layer;
wherein
said first and second elastic members crossover one another at crossover sites which are located on transversely opposite sides of said liquid-absorbent layer; and
said first and second elastic members are permanently bonded at the crossover sites to the non-stretchable auxiliary sheet; and
wherein
the respective intermediate segments of said first and second elastic members are free of direct attachment to said liquid-absorbent layer; and
wherein
the intermediate segments of said first and second elastic members are located between and connect the crossover sites located on the transversely opposite sides of said liquid-absorbent layer; and
the intermediate segments of said first and second elastic members are free of direct attachment to said non-stretchable auxiliary sheet.

2. The wearing article defined by claim 1, wherein a color of said first and second elastic members is substantially the same as that of said inner and outer sheets.

3. The wearing article defined by claim 1, wherein a stretch ratio of the respective intermediate segments of said first and second elastic members is in a range of 1.1 to 1.3.

4. The wearing article defined by claim 1, wherein said inner and outer sheets are formed from one of (i) moisture-pervious but liquid-impervious plastic film and (ii) a hydrophobic fibrous nonwoven fabric.

5. The wearing article defined by claim 1, wherein a color difference between (i) each of said inner and outer sheets and (ii) said first and second elastic members is in a range of 10 to 30 according to the following equation $$\Delta E1 = \sqrt{(L1-L2)^2 + (A1-A2)^2 + (B1-B2)^2}$$

where
$\Delta E1$ is the color difference;
L1 is a parameter representing a brightness of the first or second elastic member;
L2 is a parameter representing a brightness of the inner or outer sheet;
A1 is a parameter representing redness and greenness of the color of the first or second elastic member;
A2 is a parameter representing redness and greenness of the color of the inner or outer sheet;
B1 is a parameter representing blueness and yellowness of the color of the first or second elastic member;
B2 is a parameter representing blueness and yellowness of the color of the inner or outer sheet.

6. The wearing article defined by claim 1, wherein said non-stretchable auxiliary sheet is permanently bonded to said inner sheet but not to said liquid-absorbent layer.

7. The wearing article defined by claim 6, wherein said first and second elastic members are permanently attached to the non-stretchable auxiliary sheet at the crossover sites while the respective intermediate segments of said first and second elastic members are in a non-stretched state, and the intermediate segments of said first and second elastic members cause substantially no contraction or wrinkles in said liquid-absorbent layer.

8. The wearing article defined by claim 1, wherein
the intermediate segments of said first and second elastic members are sandwiched between the non-stretchable auxiliary sheet and said liquid-absorbent layer.

9. The wearing article defined by claim 8, wherein the non-stretchable auxiliary sheet, said first and second elastic members, and said inner and outer sheets have substantially the same color.

10. The wearing article defined by claim 1, wherein
the intermediate segments of said first and second elastic members are sandwiched between the non-stretchable auxiliary sheet and said inner sheet; and
the intermediate segments of said first and second elastic members are free of direct attachment to said inner sheet.

11. The wearing article defined by claim 10, wherein said first and second elastic members are permanently bonded at the crossover sites to the inner sheet.

12. The wearing article defined by claim 1, wherein said non-stretchable auxiliary sheet is elongated in the transverse direction and has a sufficient dimension in the longitudinal direction to cover the crossover sites and the intermediate segments of said first and second elastic members.

13. The wearing article defined by claim 12, wherein
each of the lateral segments of said first and second elastic members extends from one of the crossover sites to an adjacent one of the transversely opposite edges of said article in a respective one of the front and rear waist regions; and
the dimension of said non-stretchable auxiliary sheet in the longitudinal direction is insufficient to cover a significant portion of each of said lateral segments of said first and second elastic members.

14. The wearing article defined by claim 12, wherein said non-stretchable auxiliary sheet and said inner sheet are moisture-pervious and liquid-impervious.

15. The wearing article defined by claim 14, wherein said non-stretchable auxiliary sheet is a translucent, non-stretchable plastic film and said inner sheet is a hydrophobic fibrous non-woven fabric.

16. The wearing article defined by claim 1, wherein intermediate segments of said first and second elastic members are closer, in the longitudinal direction, to the front waist region than the rear waist region.

17. The wearing article defined by claim 5, wherein a first color difference between said inner sheet and a standard white plate is higher than a second color difference between said outer sheet and the standard white plate according to the following equation $$E2=\sqrt{(L0-L2)^2+(A0-A2)^2+(B0-B2)^2}$$

where
E2 is the first or second color difference;
L0 is a parameter representing a brightness of the standard white plate;
A0 is a parameter representing redness and greenness of the color of the standard white plate;
B0 is a parameter representing blueness and yellowness of the color of the standard white plate.

18. A disposable wearing article, comprising:
a topsheet adapted to face a wearer's skin;
a backsheet adapted to face away from the wearer's skin;
a liquid-absorbent layer sandwiched between said topsheet and backsheet;
a front waist region;
a rear waist region;
a crotch region extending in a longitudinal direction of the article between said waist regions;
longitudinally opposite ends extending in a transverse direction of the article and transversely opposite edges extending in the longitudinal direction;
stretchable and contractible first and second leg elastic members;
each of said first elastic members defining a first curve convex toward said rear waist region and having
two opposite lateral segments extending from the transversely opposite edges in said front waist region, respectively, into said crotch region, and
an intermediate segment extending between said lateral segments of said first elastic member and across said liquid-absorbent layer;
each of said second elastic members defining a second curve convex toward said front waist region and having
two opposite lateral segments extending from the transversely opposite edges in said rear waist region, respectively, into said crotch region, and
an intermediate segment extending between said lateral segments of said second elastic member and across said liquid-absorbent layer; and
a non-stretchable auxiliary sheet sandwiched between the backsheet sheet and the liquid-absorbent layer;
wherein
said first and second elastic members crossover one another at crossover sites which are located on transversely opposite sides of said liquid-absorbent layer;
said first and second elastic members are permanently bonded at the crossover sites to the non-stretchable auxiliary sheet;
said non-stretchable auxiliary sheet is elongated in the transverse direction and has a sufficient dimension in the longitudinal direction to cover the crossover sites and the intermediate segments of said first and second elastic members;
the intermediate segments of said first and second elastic members are sandwiched between said liquid-absorbent layer and said backsheet;
the intermediate segments of said first and second elastic members are located between and connect the crossover sites located on the transversely opposite sides of said liquid-absorbent layer; and
the intermediate segments of said first and second elastic members are free of direct attachment to said non-stretchable auxiliary sheet, said liquid-absorbent layer and said backsheet.

* * * * *